United States Patent [19]

Gorski

[11] Patent Number: 5,193,396
[45] Date of Patent: Mar. 16, 1993

[54] TENSILE TESTING APPARATUS
[75] Inventor: Bernard P. Gorski, Nepean, Canada
[73] Assignee: Her Majesty the Queen in right of Canada, Canada
[21] Appl. No.: 765,263
[22] Filed: Sep. 25, 1991
[51] Int. Cl.[5] ............................................. G01N 3/08
[52] U.S. Cl. ...................................................... 73/831
[58] Field of Search .................. 73/818, 831, 833, 859, 73/860, 796, 798, 859

[56] References Cited

U.S. PATENT DOCUMENTS

| | | | |
|---|---|---|---|
| 2,697,938 | 12/1954 | Tanaka | 73/94 |
| 3,107,524 | 10/1963 | O'Connor | 73/860 |
| 3,481,190 | 12/1969 | Inoue | 73/796 |
| 3,593,573 | 7/1971 | Ely | 73/94 |
| 3,992,928 | 11/1976 | Thoms . | |
| 4,686,860 | 8/1987 | Liu | 73/856 |
| 4,866,992 | 9/1989 | Rice | 73/856 |

FOREIGN PATENT DOCUMENTS 144564 11/1980 Japan ..................................... 73/796

OTHER PUBLICATIONS

"Elements of Strength of Materials" Timoshenko et al. D. Van Nostrand Company, Inc. Princeton, NJ ©1962 pp. 308-311.

Primary Examiner—Jerry W. Myracle
Attorney, Agent, or Firm—Jones, Tullar & Cooper

[57] ABSTRACT

The invention relates to a device for use in the direct tensile testing of materials, in particular brittle materials, which is self-centering under eccentrically applied loads. The apparatus effectively communicates a compressive load applied thereto to a tensile load applied substantially concentrically to the pull axis of the test specimen and thus can be employed to obtain direct tensile test characteristics by utilizing devices capable of exerting compressive forces only. In one embodiment, the apparatus comprises a pair of grips for gripping the specimen which are pivotally attached at right angles to respective sleeves in a dual sleeve assembly. The sleeves are movable so as to self-center the load which is applied, thereby eliminating bending stresses associated with off-centered loading and thus providing more accurate test results.

22 Claims, 1 Drawing Sheet

TENSILE TESTING APPARATUS

BACKGROUND

The invention relates to a device for facilitating the testing of tensile properties of materials and, in particular, to an apparatus which can be used to test the tensile characteristics of a materials utilizing a compressive load.

The accuracy of tensile test results are highly dependent upon reduction or elimination of secondary stresses induced in the specimen during the test procedure. The reduction or elimination of these secondary stresses provides test results which are more easily analyzed as failure is less likely to be attributable to non-tensile failure factors. In testing the tensile strength of brittle materials, such as rock, the reduction of secondary stresses is critical. The application of tensile loads to rock introduces difficulties in gripping the specimens without damaging the surface, in applying the load concentric with the axis of the specimen to prevent bending of the sample, and in avoiding abnormal stress concentrations at the grip ends.

Various methods for tensile testing of rock and other brittle materials have come into practice. Some involve the use of universal joints, flexible cables or similar mechanisms to obtain concentric load transfer while others involve the use of different bonding media at the gripping ends to eliminate stress concentrations associated with clamping. These direct methods rely on either very elaborate and time-consuming sample preparation or the use of highly specialized equipment. Such requirements have led to the development of indirect methods of approximating tensile strength. Of the known indirect methods, the Brazilian disc test is one of the most commonly used in the field of rock mechanics due to the ease of sample preparation and set-up. The sample consists of a disc of rock cut from a core and having a length to diameter ratio of 1:2. The specimens are loaded to failure at diametrically opposed surfaces using a compression press. The test is based on the experimental fact that most rocks in biaxial stress fields fail in tension at their tensile strength when one principal stress is tensile and the other finite principal stress is compressive with a magnitude not exceeding three times that of the tensile principal stress. Although there is some doubt as to the accuracy and even the validity of the Brazilian test, it continues to be used as a common tensile approximation, even though the direct-pull methods are considered to be most accurate. Unfortunately, laboratories equipped only with compression testing machines and/or having limited financial resources must rely on such indirect methods.

SUMMARY OF THE INVENTION

The present invention overcomes the afore-mentioned drawbacks by providing a relatively inexpensive, self-aligning apparatus for facilitating the tensile testing of brittle materials. The apparatus effectively communicates a compressive load applied to the apparatus to a tensile load applied substantially concentric with the longitudinal axis of the test specimen and thus can be utilized in conjunction with devices capable of exerting compressive forces only. Secondary stresses in the specimen due to bending are eliminated as the apparatus is self-centring under eccentrically applied loads.

More specifically, there is provided an apparatus for use in the tensile testing of a specimen which comprises a first grip means for gripping one end of the specimen, a second grip means for gripping the opposite end of the specimen, a first intermediate member having a load bearing portion, and a second intermediate member also having a load bearing portion. The first and second intermediate members are disposed such that the load bearing portions are generally outwardly opposed. A first transversely extending means pivotally connects the first grip means to the first intermediate member and a second transversely extending means, disposed substantially orthogonal to the first transversely extending means, pivotally connects the second grip means to the second intermediate member. When a compressive load is applied to the load bearing portions of the first and second intermediate members, it is transposed to a tensile load applied to the specimen.

The apparatus is relatively inexpensive to manufacture and easy to assemble. Research facilities and small laboratories equipped only with compression-type presses may employ the device for directly testing the tensile properties of materials without having to resort to indirect testing methods.

DETAILED DESCRIPTION OF THE PREFERRED EMBODIMENT

Figure 1:
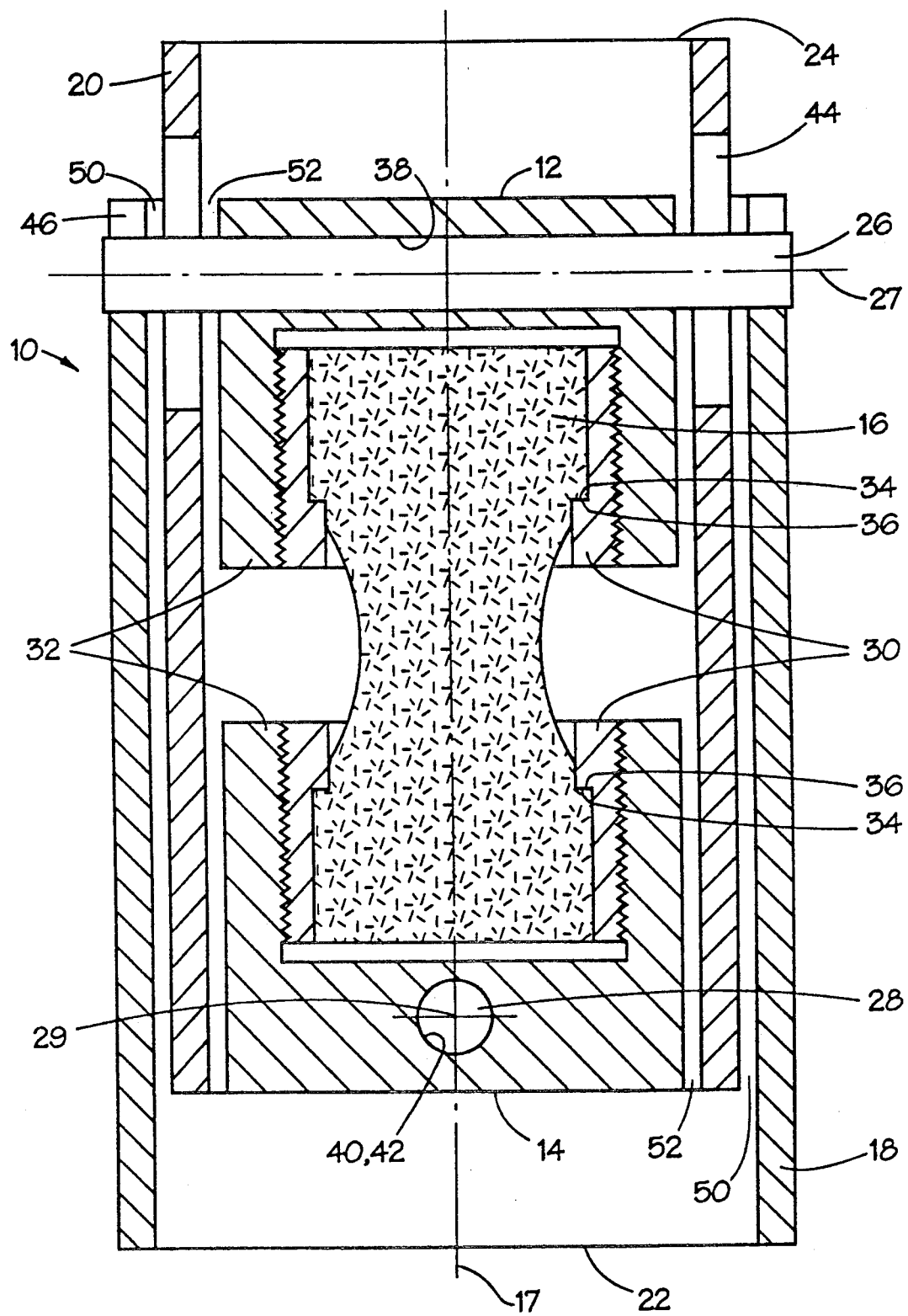
FIG. 1 is a cross-sectional view of the preferred embodiment of the invention.

FIG. 1 illustrates the preferred embodiment of the tensile testing apparatus indicated generally by reference numeral 10. The apparatus 10 comprises a pair of grips 12, 14 which grip the ends of the specimen 16, and a pair of intermediate members 18, 20 which indirectly cooperate with the grips 12, 14 through pivotal connections to transpose the load from a compressive force applied to the apparatus 10 to a tensile force applied to the specimen 16. Preferably, the intermediate members 18, 20 are cylindrical sleeves, the inner sleeve 20 being receivable within the outer sleeve 18. The outer and inner sleeves 18, 20 have opposed load bearing ends 22, 24, respectively, adapted to cooperate with the load exerting members of a compression device (not shown). In the embodiment shown in FIG. 1, transversely extending resist pins 26, 28 pivotally connect the intermediate members 18, 20 with grips 12, 14, respectively. The resist pins 26, 28 are preferably disposed at 90° relative to one another. This allows the specimen/grip assembly to swivel axially in line with the load, thereby eliminating any bending stresses induced by off-centered loading. The directional transposition of the applied load (i.e. compressive to tensile) is accomplished by an overlapping arrangement of the intermediate members 18, 20 wherein the load is effectively applied to the remote or distal ends of the specimen 16, thereby placing the specimen in tension. In the embodiment shown in FIG. 1, the outer and inner sleeves 18, 20 telescopically overlap generally in the area of the specimen 16. A compressive load applied at the load bearing ends 22, 24 is transmitted through the outer and inner sleeves 18, 20 and by means of resist pins 26, 28 to the grips 12, 14, respectively. The grips 12, 14 act upon the specimen 16 so as to try to pull the specimen 16 apart axially.

Preferably, grips 12, 14 are of the split collar type comprising externally threaded split collars 30 which are retained on the ends of said specimen by internally threaded nuts 32. In order to ensure perfection in the alignment of the specimen 16, the collars 30 are split then machined and threaded as a single piece. The collars 30 may be made to conform to the shape of the specimen or the specimen may be machined to conform to the shape of the collars.

It will be appreciated that the configuration of the specimen 16 shown in the drawing is intended to be illustrative rather than limiting and that alternate geometries could be tested using similar or different gripping systems than that shown. Preferably, the grips 12, 14 do not exert any significant radial compressive forces on the ends of the specimen. In the embodiment shown in FIG. 1, collars 30 are provided with an annular shoulder 34 which mates with a corresponding shoulder 36 provided on specimen 16. Preferably, the surfaces of shoulders 34 lie substantially in parallel planes which are parallel to the pivot axes 27, 29 formed by respective resist pins 26, 28 when the apparatus 10 is assembled and the shoulders 36 lie substantially in parallel planes which are normal to the longitudinal or pull axis 17 of specimen 16. This will ensure that the load which is transmitted to the pins 26, 28 will act coaxially with respect to specimen axis 17.

While there has been shown and described but one system for gripping the specimen 16, it is not intended to be limiting and it will be appreciated that various other arrangements known in the art may alternatively be used for gripping the specimen. Ideally, the gripping of the specimen should be such as to induce little or no secondary stresses in the specimen. Where these stresses are unavoidable, it is desirable that the resultant stress acts generally concentrically with respect to the specimen.

In order to facilitate assembly of the apparatus 10, the grips 12, 14 are provided with transversely extending bores 38, 40 which are adapted to receive resist pins 26, 28, respectively. Preferably, the bores 38, 40 are located such that when the grips 12, 14 are arranged on the ends of specimen 16, the axis 17 of the specimen 16 passes diametrically through both. Resist pins 26, 28 extend sufficiently outward so as to engage pin end accommodating means provided in the outer and inner sleeves 12, 14. In the embodiment illustrated in FIG. 1, pin 28 is engageable with diametrically opposed holes 42 provided in inner sleeve 20 and pin 26 is engageable with diametrically opposed U-shaped slots 46 provided in outer sleeve 18. Depending on the configuration of the intermediate member 20, it might be necessary to make provisions to allow pin 26 to pass through portions thereof. With a cylindrical inner sleeve as shown in FIG. 1, these provisions preferably comprise diametrically opposed, longitudinally extending apertures or slots 44 which not only allow the resist pin 26 to pivotally connect the grip 12 with the outer sleeve 18, but also allow the inner sleeve 20 to pivot about axis 27 relative to the outer sleeve 18, to pivot about axis 29 relative to the grip/specimen assembly, and to translate longitudinally with respect to the specimen 16 in response to the application of a compressive load.

One method of assembly of the apparatus 10 for conducting tensile tests is as follows. The specimen 16 is prepared in accordance with known methods. The mating split collars 30 are positioned on the ends of the specimen 16 and are then threaded as a unit into grip nuts 32. The grip/specimen assembly is disposed within inner sleeve 20 such that the hole 40 is aligned with diametrically opposed holes 42 in the inner sleeve 20 and the pin 28 is slid therethrough. This pivot connection allows the inner sleeve 20 to pivot about axis 29 relative to the grip/specimen assembly. The bore 38 is aligned with longitudinally extending slots 44 in the inner sleeve 20. Resist pin 26 is slid through one of the slots 44, and through bore 38 in grip 12 so that it projects through the other of the slots 44. This assembly is then positioned within the outer sleeve 18 such that resist pin 26 is journalled on half-slots 46 provided in outer sleeve 18. While diametrically opposed holes could be employed in place of the U-shaped slots 46 in order to accommodate the ends of pin 26, such holes would make assembly of the apparatus 10 more difficult as alignment of these holes with slots 44 and bore 38 would have to be achieved prior to insertion of the pin 26. As mentioned above, the resist pins 26 and its associated slots 44 and U-shaped slots 46 are disposed orthogonal to resist pin 28 and its associated holes 42 and, in this regard, the bores 38, 40 in the grips 12, 14 should be positioned at right angles when threaded onto their respective split collars 30.

Sufficient clearances 50, 52 are provided between outer and inner sleeves 18, 20 and between inner sleeve 20 and grips 12, 14, respectively, so as to not unduly restrict the self-centring capability of the apparatus 10. These clearances 50, 52 also provide passageways for confining fluid when the specimen is to be tested under triaxial conditions or elevated temperatures.

While there has been shown and described herein the preferred embodiment of a tensile testing apparatus, it should be recognized that various modifications may be effected without departing from the spirit and scope of the invention. For example, instead of utilizing intermediate members 18, 20 in their form illustrated and described, it will be appreciated that the load exerting members of the compression device may be suitably adapted to provide some or all of the functions thereof. In addition, there exists numerous alternate means by which pivotal connections can be made between the grips and the associated intermediate members to achieve the self-aligning characteristic of the present invention. These and other variants are encompassed within the appended claims.

What is claimed is:

1. An apparatus for use in the tensile testing of a specimen comprising:

a first grip means for gripping one end of said specimen;

a second grip means for gripping the opposite end of said specimen;

a first intermediate member having a load bearing portion;

a second intermediate member having a load bearing portion, said first and second intermediate members being disposed such that said load bearing portions are generally outwardly opposed;

first means including a first resist pin receivable within a transversely extending bore within said first grip means, said first pin being of sufficient length so as to project radially outwardly when positioned within said first grip means bore to engage pin end accommodating means provided on said first intermediate member for pivotably connecting said first grip means with said first intermediate member; and second means including a second resist pin receivable within a transversely extending bore within said second grip means, said second pin being of sufficient length so as to project radially outwardly when positioned within said second grip means bore to engage pin end accommodating means provided on said second intermediate member for pivotally connecting said second grip means with said second intermediate member, said first and second means being disposed substantially orthogonal to one another and substantially transversely with respect to said specimen such that a compressive load, when applied to said load bearing portions of said first and second intermediate members, is transposed to a tensile load applied to said specimen.

2. The apparatus as claimed in claim 1, wherein said pin end accommodating means on said first intermediate member comprises opposed holes of sufficient size to accommodate the ends of said first pin.

3. The apparatus as claimed in claim 1, wherein said pin end accommodating means on said second intermediate member comprises opposed U-shaped slots of sufficient size to accommodate the ends of said second pin.

4. The apparatus as claimed in claim 1, wherein said first and second intermediate members are cylindrical sleeves of differing diameters, the first being receivable generally axially within the second.

5. The apparatus as claimed in claim 1, wherein said first and second grip means each comprise a split collar engageable with the end of said specimen and means for retaining said split collar thereon.

6. The apparatus as claimed in claim 5, wherein said split collar is externally threaded and wherein said retaining means is an internally threaded nut engageable with said split collar.

7. The apparatus as claimed in claim 6, wherein said collar is provided with a shoulder adapted to engage axially a corresponding shoulder provided on said specimen end.

8. In combination with a compression device having load exerting members, an apparatus for use in the tensile testing of a specimen comprising:
   a first grip means for gripping one end of said specimen;
   a second grip means for gripping the opposite end of said specimen;
   a first intermediate member;
   a second intermediate member, said first and second intermediate members being cylindrical sleeves of differing diameters, the first being receivable generally axially within the second and having means adapted to cooperate with said load exerting members of said compression device;
   first means for pivotally connecting said first grip means with said first intermediate member; and
   second means for pivotally connecting said second grip means to said second intermediate member, said first and second means being disposed substantially orthogonal to one another and substantially transversely with respect to said specimen such that a compressive load, when applied to said first and second intermediate members, is transposed to a tensile load applied to said specimen.

9. The apparatus as claimed in claim 8, wherein said compression device is a compression press.

10. The apparatus as claimed in claim 8, wherein said compression device is a triaxial compression chamber.

11. The apparatus as claimed in claim 8, wherein said first means comprises a first resist pin receivable within a transversely extending bore within said first grip means, said first pin being of sufficient length so as to project radially outwardly when positioned within said first grip means bore to engage pin end accommodating means provided on the inner sleeve and wherein said second means comprises a second resist pin receivable within a transversely extending bore within said second grip means, said second pin being of sufficient length so as to project radially outwardly when positioned within said second grip means bore to engage pin end accommodating means provided on the outer sleeve, and aperture means provided in said first intermediate member through which said second pin extends to said outer sleeve.

12. The apparatus as claimed in claim 8, wherein said first and second grip means each comprise a split collar engageable with the end of said specimen and means for retaining said split collar thereon.

13. An apparatus for use in the tensile testing of a specimen comprising:
   a first grip means for gripping one end of said specimen;
   a second grip means for gripping the opposite end of said specimen;
   an inner cylindrical member having a load bearing end;
   an outer cylindrical member having a load bearing end, said inner member being receivable generally axially within said outer member such that said load bearing ends of said members are generally outwardly opposed, said first and second grip means being receivable generally axially within said inner member;
   first means for pivotally connecting said first grip means to said first intermediate member at or near the end thereof opposite its load bearing end;
   second means for pivotally connecting said second grip means to said second intermediate member at or near the end thereof opposite its load bearing end, said second means including diametrically opposed aperture means provided in said inner member through which said connection can be effected;
   said first and second means being disposed substantially orthogonal to one another and substantially transversely with respect to said specimen such that a compressive load, when applied to said load bearing portions of said first and second intermediate members, is transposed to a tensile load applied to said specimen.

14. The apparatus as claimed in claim 13, wherein said first means comprises a first resist pin receivable within a transversely extending bore within said first grip means, said first pin being of sufficient length so as to project radially outwardly when positioned within said first grip means bore to engage pin end accommodating means provided on said inner sleeve and wherein said second means comprises a second resist pin receivable within a transversely extending bore within said second grip means, said second pin being of sufficient length so as to project radially outwardly when positioned within said second grip means bore to engage pin end accommodating means provided on said outer sleeve.

15. The apparatus as claimed in claim 13, wherein said first and second grip means each comprise a split collar engageable with the end of said specimen and means for retaining said split collar thereon.

16. The apparatus as claimed in claim 15, wherein said collar is provided with a shoulder adapted to engage axially a corresponding shoulder provided on said specimen end.

17. An apparatus for use in the tensile testing of a specimen comprising:
- a first grip means for gripping one end of said specimen;
- a second grip means for gripping the opposite end of said specimen;
- a first intermediate member having a load bearing portion;
- a second intermediate member having a load bearing portion, said first and second intermediate members being cylindrical sleeves of differing diameters, the first being receivable generally axially within the second, and further being disposed such that said load bearing portions are generally outwardly opposed;
- first means for pivotally connecting said first grip means with said first intermediate member; and
- second means for pivotally connecting said second grip means with said second intermediate member, said first and second means being disposed substantially orthogonal to one another and substantially transversely with respect to said specimen such that a compressive load, when applied to said load bearing portions of said first and second intermediate members, is transposed to a tensile load applied to said specimen.

18. The apparatus as claimed in claim 17, wherein said first means comprises a first resist pin receivable within a transversely extending bore within said first grip means, said first pin being of sufficient length so as to project radially outwardly when positioned within said first grip means bore to engage pin end accommodating means provided on the inner sleeve and wherein said second means comprises a second resist pin receivable within a transversely extending bore within said second grip means, said second pin being of sufficient length so as to project radially outwardly when positioned within said second grip means bore to engage pin end accommodating means provided on the outer sleeve, and aperture means provided in said first intermediate member through which said second pin extends to said outer sleeve.

19. The apparatus as claimed in claim 18, wherein said aperture means comprises diametrically opposed, longitudinally extending slots.

20. The apparatus as claimed in claim 17, wherein said first and second grip means each comprise a split collar engageable with the end of said specimen and means for retaining said split collar thereon.

21. The apparatus claimed in claim 20, wherein said split collar is externally threaded and wherein said retaining means is an internally threaded nut engageable with said split collar.

22. The apparatus as claimed in claim 21, wherein said collar is provided with a shoulder adapted to engage axially a corresponding shoulder provided on said specimen end.

* * * * *